United States Patent [19]

Babin et al.

[11] Patent Number: 5,530,022
[45] Date of Patent: Jun. 25, 1996

[54] ESTERS OF 2,2-DIMETHYL-3-(3,3,3-TRIFLUORO-1-PROPENYL)-CYCLOPROPANE CARBOXYLIC ACID

[75] Inventors: Didier Babin, Montigny; Marc Benoit, Roquevaire; Jean P. Demoute, Neuilly-Plaisance, all of France

[73] Assignee: Roussel-Uclaf, France

[21] Appl. No.: 287,839

[22] Filed: Aug. 9, 1994

[30] Foreign Application Priority Data

Aug. 10, 1993 [FR] France .................. 93 09804

[51] Int. Cl.[6] .................. A61K 31/34; C07D 307/02
[52] U.S. Cl. .................. 514/461; 514/531; 514/690; 549/500; 558/434; 560/124
[58] Field of Search .................. 560/124; 558/434; 549/500; 514/461, 531, 690

[56] References Cited

U.S. PATENT DOCUMENTS

| | | | |
|---|---|---|---|
| 4,238,505 | 12/1990 | Engel | 424/305 |
| 4,332,815 | 6/1992 | Engel | 424/274 |
| 4,457,940 | 7/1984 | Katsuda et al. | 424/274 |

FOREIGN PATENT DOCUMENTS

| | | |
|---|---|---|
| 0003336 | 8/1979 | European Pat. Off. . |
| 0031199 | 7/1981 | European Pat. Off. . |
| 0253536 | 1/1988 | European Pat. Off. . |
| 2392964 | 12/1978 | France . |
| 1052119 | 12/1966 | United Kingdom . |
| 1336230 | 11/1973 | United Kingdom . |
| WO/01368 | 4/1982 | WIPO . |

OTHER PUBLICATIONS

Engel 'Insecticidal perhaloalkyl vinyl-cyclopropane carboxylates' CA 98:72491 (1979).

*Primary Examiner*—Amelia Owens
*Attorney, Agent, or Firm*—Bierman & Muserlian

[57] ABSTRACT

A compound in all possible stereoisomeric forms and their mixtures of the formula

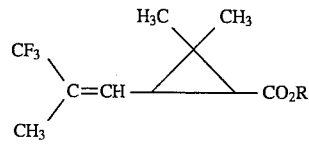

wherein R is selected from the group consisting of

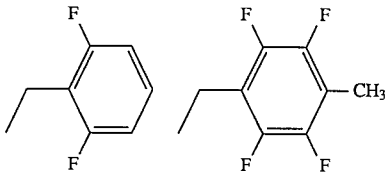

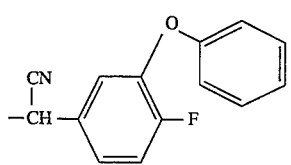

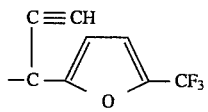

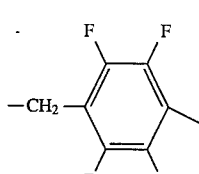

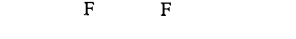

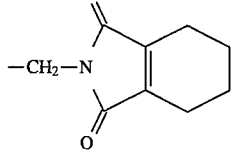

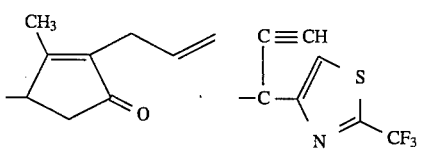

having excellent pesticidal, particularly insecticidal, properties.

14 Claims, No Drawings

ESTERS OF 2,2-DIMETHYL-3-(3,3,3-TRIFLUORO-1-PROPENYL)-CYCLOPROPANE CARBOXYLIC ACID

OBJECTS OF THE INVENTION

It is an object of the invention to provide the novel compounds of formula I and a process for their preparation.

It is another object of the invention to provide novel pesticidal compositions and a method of combatting pests.

These and other objects and advantages of the invention will become obvious from the following detailed description.

THE INVENTION

The novel compounds of the invention are compounds in all possible stereoisomeric forms and their mixtures of the formula

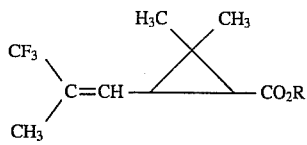

wherein R is selected from the group consisting of

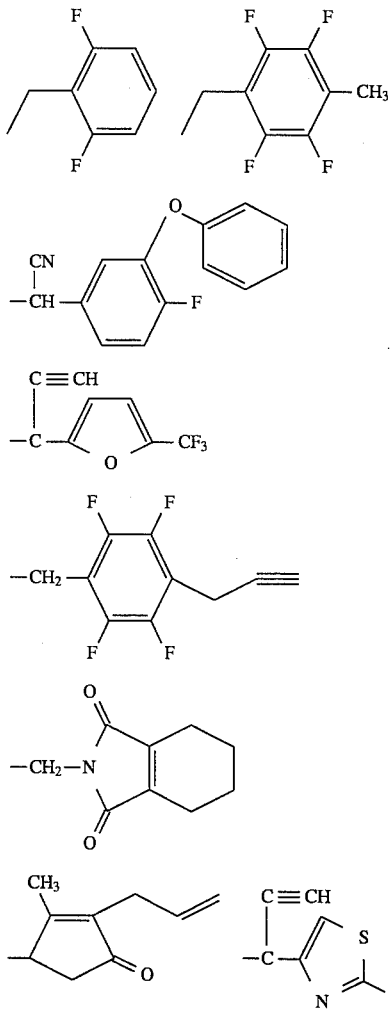

Preferred compounds of formula I are those wherein the cyclopropane copula has 1R, cis structure, those wherein the geometry of the double bond is E, those wherein R is 4-methyl-2,3,5,6-tetrafluoro-benzyl, 4-(2-propyn-1-yl)-2,3,5,6-tetrafluorobenzyl, 1-[5-trifluoromethyl-2-furyl]-2-propynyl or α-cyano-3-phenoxy-4-fluoro-benzyl.

The process for the preparation of the compounds of formula I comprises reacting an acid of the formula

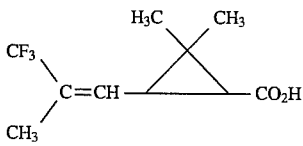

or a functional derivative thereof with an alcohol of the formula

R-OH     III wherein R has the above definition or a functional derivative thereof to form the compound of formula I.

The functional derivative of the acid used is preferably an acid chloride. When the acid of formula II and the alcohol of formula III are reacted, the operation is preferably carried out in the presence of dicyclohexylcarbodiimide. The preparation of [1R(1α,3α)]-2, 2-dimethyl-3-[(E)-2-methyl-3,3,3-trifluoro-1-propenyl]-cyclopropane-carboxylic acid is given in the examples.

The different alcohols used are known products and α-ethynyl2-(trifluoromethyl)-4-thiazole-methanol can be prepared as indicated in European Patent Application No. 0,556,123.

The pesticidal compositions of the invention are comprised of a pesticidally effective amount of a compound of formula I and an inert carrier. The compositions are useful for combatting parasites such as parasites of vegetation, parasites of premises and parasites of warm-blooded animals and are used to combat parasitic insects, nematodes and acaridae of vegetation and animals.

A particular subject of the invention is the use of the compositions of compounds of formula I for combatting parasites of vegetation, parasites of premises and parasites of warm-blooded animals. The compositions can also be used to combat insects and other parasites of the soil, for example Coleoptera such as Diabrotica, click beetles and May beetle grubs, Myriapoda such as scutigeridae and blanjules, and Diptera such as cecydomia and Lepidoptera such as owlet moths. They are used at doses comprised between 10 g and 300 g of active ingredient per hectare.

The compositions can also be used to combat insects in premises, to combat particularly flies, mosquitoes and cockroaches.

Moreover, the products of formula I are photostable and are not very toxic to mammals. All of these properties mean that the products of formula I correspond perfectly to the requirements of the modern agrochemical industry; they allow crops to be protected while preserving the environment.

The compositions can also be used to combat parasitic acaridae and nematodes of vegetation and can also be used to combat parasitic acaridae of animals, to combat for example ticks and notably ticks of the Boophilus species, those of the Hyalomnia species, those of the Amblyomnia species and those of the Rhipicephalus species or to combat all types of mites and notably the sarcoptic mite, the psoroptic mite and the chorioptic mite.

The compositions are intended to combat parasites of vegetation, parasites of premises and parasites of warm-blooded animals, provided that they contain at least one of the products of formula I defined above.

A particular subject of the invention is the insecticide compositions containing as active ingredient at least one of the products of formula I, particularly, insecticide compositions intended to combat Diabrotica and other parasites of the soil. These compositions are prepared according to the usual processes of the agrochemical industry or the veterinary industry or the industry for products intended for animal nutrition.

In the compositions intended for agricultural use and use in premises, the active ingredient or ingredients can optionally have added thereto one or more pesticide agents. These compositions can be in the form of powders, granules, suspensions, emulsions, solutions, aerosol solutions, combustible strips, baits or other preparations usually employed for the use of these types of compounds.

In addition to the active ingredient, these compositions generally contain a vehicle and/or a non-ionic surfactant, ensuring a uniform dispersion of the substances of the mixture. The vehicle used can be a liquid such as water, alcohol, hydrocarbons or other organic solvents, a mineral, animal or vegetable oil, a powder such as talc, clays, silicates, kieselguhr or a combustible solid. The insecticide compositions of the invention preferably contain from 0.005% to 10% by weight of active ingredient.

According to an advantageous operating method for a use in premises, the compositions of the invention are used in the form of fumigant compositions which can then be advantageously constituted, for the non-active part, by a combustible insecticide coil, or also by an incombustible fibrous substrate. In the latter case, the fumigant obtained after incorporation of the active ingredient is placed on a heating apparatus such as an electric vaporizer. In the case where an insecticide coil is used, the inert support can be, for example, pyrethrum marc compound, Tabu powder (*Machilus thumbergii* leaf powder), pyrethrum stem powder, cedar leaf powder, sawdust (such as pine sawdust), starch and coconut shell powder. The dose of active ingredient can be, for example, for 0.03 to 1% by weight. In the case where an incombustible fibrous support is used, the dose of active ingredient can be, for example from 0.03 to 95% by weight.

The compositions of the invention for use in premises can also be obtained by preparing a sprayable oil based on the active ingredient, the oil impregnating the wick of a lamp and then being set alight. The concentration of active ingredient incorporated in the oil is preferably 0.03 to 95% by weight.

Also a subject of the invention are the acaricide and nematicide compositions containing as active ingredient at least one of the products of formula I defined above. The insecticide and nematicide compositions can optionally have added to them one or more other pesticide agents. The acaricide and nematicide compositions can be particularly in the form of powder, granules, suspensions, emulsions and solutions.

For acaricide use, wettable powders are preferably used for foliar spraying containing 1 to 80% by weight of active ingredient, or liquids for foliar spraying containing 1 to 500 g/l of active ingredient. Powders for foliar dustings can also be used containing 0.05 to 3% of active ingredient.

For nematicide use, liquids are preferably used for soil treatment containing 300 to 500 g/l of active ingredient. The acaricide and nematicide compositons of the invention are used preferably at doses comprised between 1 and 100 g of active ingredient per hectare.

To enhance the biological activity of the products of the invention, they can have added to them the standard synergists used in such a case as such 1-(2,5,8-trioxadodecyl)-2-propyl-4,5-methylene-dioxy-benzene (or piperonyl-butoxide) or N-(2-ethyl-heptyl)-bicyclo-[2, 2-1]-5-heptene-2,3-carboximide, or piperonyl-bis-2-(2'-n-butoxy-ethoxy)-ethylacetal (or tropital).

The compounds of formula I have an excellent general tolerance, and therefore are also useful for combating in particular illnesses caused by ticks and mites in man and animals. The products of the invention are particularly used to combat lice as a preventive or curative and to combat scabies.

The composition of the invention can be administered externally by spraying, by shampooing, by bathing or painting on. The compositions of the invention for veterinary use can also be administered by painting on the spine according to the so-called "pour-on" method. The composition of the invention can also be used as biocides or as growth regulators.

The compositions endowed with insecticide, acaricide or nematicide activity may contain as active ingredient besides at least one of the compounds of formula I, at least one of the pyrethrinoid esters selected from the group consisting of the esters of allethrolone, of 3,4,5,6-tetrahydrophthalimidomethyl alcohol, of 5-benzyl-3-furyl-methyl alcohol, of 3-phenoxybenzyl alcohol and of α-cyano-3-phenoxybenzyl alcohol with chrysanthemic acids, by the esters of 5-benzyl-3-furyl-methyl alcohol with 2,2-dimethyl-3-(2-oxo-3-tetrahydrothiophenylidenemethyl)cyclopropanecarboxylic acids, by the esters of 3-phenoxybenzyl alcohol and of α-cyano-3-phenoxybenzyl alcohol with 2,2-dimethyl-3(2,2-dichlorovinyl)-cyclopropanecarboxylic acids, by the esters of α-cyano-3-phenoxy-benzyl alcohol with 2,2-dimethyl-3-(2,2-dibromovinyl)-cyclopropanecarboxylic acids, by the esters of 3phenoxybenzyl alcohol with 2-parachlorophenyl-2-isopropyl acetic acids, by the esters of allethrolone, of 3,4,5,6-tetrahydrophthalimidomethyl alcohol, of 5-benzyl-3-furyl methyl alcohol, of 3-phenoxybenzyl alcohol, and of α-cyano-3-phenoxybenzyl alcohol with 2,2-dimethyl-3-(1, 2,2,2-tetrahaloethyl)-cyclopropanecarboxylic acids, in which "halo" represents a fluorine, chlorine or bromine, it being understood that the compounds of formula I can exist in all their possible stereoisomeric forms, as well as the acid and alcohols copulas of the above pyrethrinoid esters.

The novel method of the invention for combating insects comprises contacting the insects with an insecticidally effective amount of a compound of formula I.

In the following examples, there are described several preferred embodiments to illustrate the invention. However, it is to be understood that the invention is not intended to be limited to the specific embodiments.

EXAMPLE 1

4-methyl-2,3,5,6-tetrafluorobenzyl [1R-[1α, 3α(E)]]-2,2-dimethyl-3-(2-methyl-3,3,3-trifluoro-1-propen-1-yl)-cyclopropane carboxylate A solution of 650 mg of dicyclohexylcarbodiimide, 10 mg of 4-dimethylamino-pyridine and 3.3 ml of methylene chloride was introduced at 0° C. into a solution of 700 mg of [1R-[1α,3α(E)]-2,2-dimethyl-3-(2-methyl-3,3,3-trifluoro-1-propen-1-yl)-cyclopropane carboxylic acid, 673 mg of 4-methyl-2,3,5,6-tetrafluorobenzyl alcohol and 10 ml of methylene chloride. The temperature was allowed to rise to 20° C. and the reaction medium was stirred for 16 hours, filtered, rinsed with methylene chloride and brought to dryness under reduced pressure to obtain 1.22 g of product which was chromatographed on silica, eluting with a hexane—isopropyl other mixture (95-5) to obtain 1.22 g of the desired product with a R$_f$=0.2.

| NMR CDCl$_3$ ppm | |
|---|---|
| 1.26(s) 1.28(s) | H of the twinned CH$_3$'s |
| 1.84d, J=1 | H of the CH$_3$ carried by the double bond |
| 1.80 to 195m | H$_1$ and H$_3$ |
| 2.29(t, J=α) | H of the 4 methyl |
| 5.19 | H of the CH$_2$ in α position of the C=O |

Using the procedure of Example 1 and starting with the corresponding alcohols, the following products were prepared.

EXAMPLE 2

2,6-difluorobenzyl [1R-[1α,3α(E)]]-2,2-dimethyl-3-(2-methyl-3, 3,3-trifluoro-1-propen-1-yl)-cyclopropane carboxylate

| NMR CDCl$_3$ ppm | |
|---|---|
| 1.24 and 1.28 | H of the twinned CH$_3$'s |
| 1.86m | H$_1$ and H$_3$ |
| 1.84 | H of the vinyl methyl |
| 5.19 | H of the CH$_2$ in α position of the C=O |
| 6.39 | vinyl H |
| 6.92 | H in positions 3 and 5 of the phenyl |
| 7.32 | H in position 4 of the phenyl |

EXAMPLE 3

α-cyano-3-phenoxy-4-fluoro-benzyl [1R-[1α,3α(E)]]-2,2-dimethyl-3-(2-methyl- 3,3,3-trifluoro-1-propen-1-yl)-cyclopropane carboxylate

| NMR CDCl$_3$ ppm | |
|---|---|
| 1.13 and 1.26 | H of the twinned CH$_3$'s |
| 1.86 m | H$_1$ of the vinyl CH$_3$ |
| 1.88 | H$_1$ |
| 2.00 | H$_3$ |
| 6.30 | ethylenic H |
| 6.35 | H of —CH—C≡N |
| 7.17; 7.28; 7.36 | aromatic H's |

EXAMPLE 4

(5-trifluoromethyl-2-furyl)-2-propynyl [1R-[1α,3α(E) ]]-2, 2-dimethyl-3-(2-methyl-3,3,3-trifluoro-1-propen-1-yl)-cyclopropane carboxylate

| NMR CDCl$_3$ ppm | |
|---|---|
| 1.26; 1.27; 1.28; 1.30 | H of the twinned methyls |
| 1.82 and 1.85 | H of the vinyl CH$_3$ |
| 2.64 | H of the ethynyl |
| 6.38 | vinyl H |
| 6.46 and 6.50 | H of the CH in α position of the triple bond |

EXAMPLE 5

4-(2-propynyl-1-yl)-2,3,5,6-tetrafluoro-benzyl [1R-(1α, 3α(E))]-2,2-dimethyl-3-(2-methyl-3,3,3-trifluoro-1-propen-1-yl)-cyclopropane carboxylate

| NMR CDCl$_3$ ppm | |
|---|---|
| 1.26 and 1.27 | H of the twinned CH$_3$'s |
| 1.83 | H of the vinyl methyl |
| 1.86 | H$_1$ and H$_3$ |
| 6.37 | ethylenic H |
| 3.64 | H of the CH$_2$ in α position of the triple bond |
| 5.20 | H |

EXAMPLE 6

1-[2-trifluoromethyl-4-isothiazoyl-2-propynyl [1R-(1α, 3α(E)]]-2, 2-dimethyl-3-(2-methyl-3,3,3-trifluoro-1-propen-1-yl )-cyclopropane carboxylate

| NMR CDCl$_3$ ppm | |
|---|---|
| 1.26(s) and 1.27(s) 1.28(s) and 1.31(s) | H of the twinned methyls |
| 1.82d, J=1 1.84d, J=1 | vinyl CH$_3$ |
| 1.93(m) | H$_1$ and H$_3$ |
| 2.68d, J=2.5 2.70d, J=2.5 | H of the triple bond |

EXAMPLE 7

3-(2-propenyl)-2-methyl-4-oxo-cyclopent-2-enyl [1R- (1α, 3α(E)]]-2,2-dimethyl-3-(2-methyl-3,3,3-trifluoro-1-propen-1-yl)-cyclopropane carboxylate

| NMR CDCl$_3$ ppm | |
|---|---|
| 1.28; 1.30 | twinned CH$_3$'s |
| 1.84 | vinyl CH$_3$ |
| 1.87 | H$_1$–H$_3$ |
| 1.99 | |
| 2.00 | H of the CH$_3$ of allethrolone |
| 2.26; 2.87 | O = C—CH$_2$—CH |

EXAMPLE 8

N-hydroxymethyl-3,4,5,6-tetrahydrophthalamide [1R-[1α, 3α(E)]]-2,2-dimethyl-3-(2-methyl-3,3, 3-trifluoro-1-propen-1-yl)-cyclopropane carboxylate melting at 102° C.

Preparation 1: [1R-[1α,3α(E)]]-2,2-dimethyl-3-(2-methyl-3,3, 3-trifluoro-1-propen-1-yl)-cyclopropane carboxylic acid.

STAGE A: methyl 3-(2-oxopropyl)-2,2-dimethyl-cyclopropane carboxylate.

10 g of 3-(2-oxopropyl)-2,2-dimethyl-cyclopropane carboxylic acid in 100 ml of acetone were heated to 30° C. to 34° C. in the presence of 7.35 g of potassium bicarbonate and 5 ml of dimethyl sulfate. After 4 hours of stirring, 0.85 ml of dimethyl sulfate were added and the reaction medium was held at 30° to 34° C. for 20 hours. After filtration, the product was taken up in ethyl ether and the solvent was evaporated. The residue was chromatographed on silica (eluant: hexane - ethyl acetate 8-2) to obtain 10.43 g of the expected product.

STAGE B: methyl 3-(2-methyl-2-trimethylsilyloxy-3,3,3-trifluoro-propyl)-2,2-dimethyl-cyclopropane carboxylate 0.5 ml of tetrabutylammonium fluoride were added at 0° C. to 5 g of the product of Stage A and 8 ml of trifluoromethyl trimethylsilane in 65 ml of tetrahydrofuran. The mixture was stirred for 15 minutes and was poured into an ice-cooled aqueous solution of potassium acid phosphate. Extraction was carried out with ethyl ether and the extracts were dried and the solvent was evaporated to obtain 7.57 g of the expected product.

STAGE C: methyl 3-(2-methyl-2-hydroxy-3,3,3-trifluoro-propyl)2,2-dimethyl-cyclopropane carboxylate 444 mg of potassium fluoride were added at ambient temperature to 500 mg of the product of Stage B in 5 ml of methanol. The reaction mixture was stirred for 3 hours, poured into 25 ml of an aqueous solution of potassium acid phosphate. Extraction was carried out with ethyl ether and the extracts were dried and the solvent was evaporated to obtain 360 mg of the expected product.

STAGE D: methyl 2,2-dimethyl-3-[(E) 2-methyl-3,3,3-trifluoro-1propenyl]-cyclopropane carboxylate 160 ml of thionyl chloride were added at 0° C. to 80.5 g of methyl 2,2-dimethyl-3-(2-methyl-2-hydroxy-3,3,3-trifluoropropylcyclopropane carboxylate of Stage C. The mixture was refluxed for 48 hours, cooled, poured into ice-cooled water and extracted with isopropyl ether. The organic phases were washed with water and after drying over magnesium sulfate and evaporation to dryness, the crude product was chromatographed on silica with a hexane-AcOEt mixture (9-1), then rechromatographed with a hexane—acetone mixture (99-1) to obtain 22.02 g of the starting alcohol, 11.71 g of the exo+Z isomer mixture and 23.31 g of the expected product.

STAGE E: [1R-(1α,3α)]-2,2-dimethyl-3-[(E)-2-methyl-3,3,3-trifluoro-1-propen-1-yl)-cyclopropane carboxylic acid 4.14 g of the product of Stage D in 52.6 ml of methanol were heated at 60° C. for 2 hours 30 minutes in the presence of 19.3 ml of N sodium hydroxide and then for 30 minutes in the presence of an additional 2 ml of N sodium hydroxide. The reaction medium was poured into ice-cooled water and extraction was carried out with isopropyl ether. The aqueous phase was acidified with $KH_2PO_4$ and extracted with isopropyl ether. These last-named phases were dried and evaporated under reduced pressure to obtain 2.94 g of the expected product.

| 1.84(s) | $CH_3$ of the double bond |
| 1.26 and 1.22(s) | twinned methyls |
| 1.3 to 1.9(m) | $H_1$ and $H_3$ |
| 6.43(m) | vinyl H. |

EXAMPLE 9

Preparation of a soluble concentrate.

A homogeneous mixture was made of 0.25 g of the Product of Example 1, 1.00 g of Piperonyl butoxide, 0.25 g of Tween 80, 0.1 g of Topanol A and 98.4 g of Water.

EXAMPLE 10

Preparation of an emulsifiable concentrate.

The following were intimately mixed 0.015 g of the Product of Example 1, 0.5 g of Piperonyl butoxide, 0.1 g of Topanol A, 3.5 g of Tween 80 and 95.885 g of Xylene.

BIOLOGICAL STUDY

A—Activity on Diabrotica

The test insects were last-stage larvae of Diabrotica and a 9 ml diameter disc of filter paper, placed at the bottom of a Petri dish, was treated with 2 ml of an acetonic solution of the product to be tested. After drying, 15 larvae per dose were deposited and a mortality check was carried out 24 hours after the treatment. From a dose of 1 ppm, the products of the invention have a good activity.

Study of the lethal effect on Spodoptera Littoralis Larvae

The tests were carried out by topical application of an acetonic solution using an Arnold micro-manipulator on the dorsal thorax of the larvae. 15 larvae were used per dose of product to be tested and the larvae used were larvae of the fourth larval stage, that is to say about 10 days old having been reared at 24° C. and 65% relative humidity. After treatment, the individuals were placed on an artificial nutritive medium (Poitout medium) and a mortality check was carried out 48 hours after treatment. The products of the invention and particularly the product of Example 3 showed useful results.

Various modifications of the products and method of the invention may be made without departing from the spirit or scope thereof and it is to be understood that the invention is intended to be limited only as defined in the appended claims.

What we claim is:

1. A compound in all possible stereoisomeric forms and their mixtures of the formula

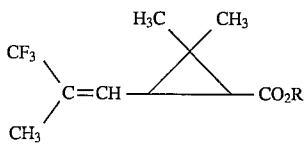

wherein R is selected from the group consisting of

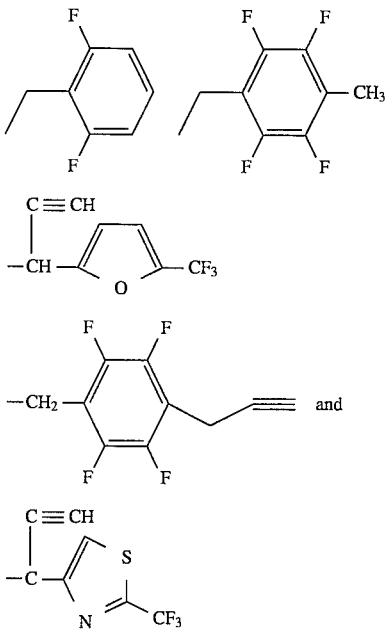

2. A compound of claim 1 wherein the cyclopropane copula is of the 1R, cis structure.

3. A compound of claim 1 wherein the geometry of the double bond is E.

4. A compound of claim 1 wherein R is [4-methyl-2,3,5,6-tetrafluoro-benzyl.

5. A compound of claim 1 wherein R is 4-(2-propyn-1-yl)-2,3,5,6-tetrafluoro-benzyl.

6. A compound of claim 1 wherein R is 1-[5-trifluoromethyl-2-furyl]-2-propynyl.

7. An insecticidal composition comprising an insecticidally effective amount of a compound of claim 1 and an inert carrier.

8. A composition of claim 7 also containing at least one of the pyrethrinoid esters selected from the group consisting of the esters of allethrolone, of 3,4,5,6-tetrahydrophthalimidomethyl alcohol, of 5-benzyl-3-furyl-methyl alcohol, of 3-phenoxybenxzyl alcohol and of α-cyano-3-phenoxybenzyl alcohol with chrysanthemic acids, by the esters of 5-benzyl-3-furyl-methyl alcohol with 2,2-dimethyl-3-(2-oxo-3-tetrahydrothiophenyl-idenemethyl)-cyclopropanecarboxylic acids, by the esters of 3-phenoxybenzyl alcohol and of α-cyano-3-phenoxybenzyl alcohol with 2,2-dimethyl-3-(2,2-dichlorovinyl)-cyclopropanecarboxylic acids, by the esters of α-cyano-3-phenoxy-benzyl alcohol with 2,2-dimethyl-3-(2,2-dibromovinyl)-cyclopropanecarboxylic acids, by the esters of 3-phenoxybenzyl alcohol with 2-parachlorophenyl-2-isopropyl acetic acids, by the esters of allethrolone, of 3,4,5,6-tetrahydrophthalimidomethyl alcohol, of 5-benzyl-3-furyl methyl alcohol, of 3-phenoxybenzyl alcohol, and of α-cyano-3-phenoxybenzyl alcohol with 2,2-dimethyl-3-(1,2,2,2-tetrahaloethyl)-cyclopropane-carboxylic acids, in which "halo" represents fluorine, chlorine or bromine, it being understood that the compounds of claim 1 can exist in all their possible stereoisomeric forms, as well as the acid and alcohols copulas of the above pyrethrinoid esters.

9. A method of combating insects comprising contacting insects with an insecticidally effective amount of a compound of claim 1.

10. The method of claim 9 wherein the cyclopropane copula is of the 1R, cis structure.

11. The method of claim 9 wherein the geometry of the double bond is E.

12. The method of claim 9 wherein R is [4-methyl-2,3,5,6-tetrafluoro-benzyl.

13. The method of claim 9 wherein R is 4-(2-propyn-1-yl)-2,3,5,6-tetrafluoro-benzyl.

14. The method of claim 9 wherein R is 1-[5-trifluoromethyl-2-furyl]-2-propynyl.

\* \* \* \* \*